United States Patent
daCosta et al.

(10) Patent No.: US 6,511,799 B1
(45) Date of Patent: Jan. 28, 2003

(54) CDX2 IS DOWNSTREAM MEDIATOR OF APC TUMOR SUPPRESSOR ACTIVITY

(75) Inventors: Luis daCosta, Columbia, MD (US); Bert Vogelstein, Baltimore, MD (US); Kenneth W Kinzler, BelAir, MD (US); Tong-Chuan He, Towson, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 09/311,551

(22) Filed: May 14, 1999

(51) Int. Cl.[7] .............................. C12Q 1/00; C12Q 1/68; G01N 33/53; C12N 5/00; C12N 5/08

(52) U.S. Cl. ................................ 435/4; 435/6; 435/21; 435/325; 435/366

(58) Field of Search ........................... 514/44; 435/325, 435/4, 6, 7.1; 424/277.1, 93.1; 436/500

(56) References Cited

U.S. PATENT DOCUMENTS 5,783,666 A * 7/1998 Albertsen et al. ........... 530/350

FOREIGN PATENT DOCUMENTS

| WO | 98/09510 | 3/1998 |
| WO | 98/41631 | 9/1998 |

OTHER PUBLICATIONS

T. Gura. Systems for identifying new drugs are ofen faulty. Science, vol. 278, pp. 1041–1042, 1997.*
Verma et al., Nature, vol. 389, p. 239–242, Sep. 1997.*
Eck et al., Goodman & Gilman's The Pharmacological Basis of Therapeutics, Ninth Edition, McGraw–Hill, New York, p. 77–101, 1996.*
Lorentz et al. "downregulation of the colon tumour–suppressor homeobo gene Cdx–2 by oncogenic ras." Oncogene, Jan. 7, 1999 18 (1) 87–92.
Refund et al. "The Cdx–1 and cdx–2 homeobox genes in the intestine." Biochemistry and cell Biology (1998) 76 (6) 957–69.
Lorentz et al "Key role of the Cdx2 homeobox gene in extracellular matrix–mediated intestinal cell differentiation" Journal of Cell Biology—Dec. 15, 1997, 139 (6) 1553–65.

He et al. "Identificaiton of C–MYC as a Target of the APC Pathway" Science, American Association for the Advancement of Science, US, vol. 281 Sep. 4, 1998 pp. 1509–1512.
Taylor et al. "Activation of enhancer elements by the homeobox gene Cdx2 is cell line specific" Nucleic Acids Research (Jun. 15, 1997) 25 (12) 2293–300.
Wicking et al. "CDX2, a human homologue of *Drosophila caudal*, is mutated in both alleles in a replication error positive colorectal cancer" Oncogene (Aug. 6, 1998) 17 (5) 657–9.
Da Costa et al. "CDX2 is mutated in a colorectal cancer with normal APC/beta–catenin signaling" Oncogene, vol. 18, No. 35, pp. 5010–5014.
Eunran Suh et al. "A Homeodomain Protein Related to caudal Regulates Intestine–Specific Gene Transcription" Molecular and Cellular Biology, Nov. 1994, pp. 7340–7351.
Suh and Traber "An Intestine–Specific Homeobox Gene Regulates Proliferation and Differentiation" Molecular and Cellular Biology, Feb. 1996, pp. 619–625.
Hooi C. Ee, "Cdx–2 Homeodomain Protein Expression in Human and Rat Colorectal Adenoma and Carcinoma" American Journal of Pathology, vol. 147, No. 3, Sep. 1995, pp. 586–591.
Carol Wicking et al. "CDX2, a human homologue of *Drosohila caudal*, is mutated in both alleles in a replication error positive colorectal cancer" Oncogene (1998) 17, pp. 657–659.
K. Chawengsaksophak et al. "Homeosis and intestinal tumours in Cdx2 mutant mice" Nature, vol. 386, Mar. 1997, pp. 84–87.
Gustavo V. Mallo et al. "Molecular Cloning, Sequencing and Expression of the mRNA encoding Human Cdx1 and Cdx2 Homeobox, Down–Regulation of Cdx1 and Cdx2 mRNA Expression During Colorectal Carcinogenesis" Int. J. Cancer (Pred. Oncol.): 74, (1997) pp. 35–44.

* cited by examiner

*Primary Examiner*—Scott D. Priebe
*Assistant Examiner*—Shin-Lin Chen
(74) *Attorney, Agent, or Firm*—Banner & Witcoff, Ltd.

(57) ABSTRACT

Human CDX2, a homeobox gene, has been identified as a downstream effector of tumor suppressor APC. APC induces the transcription of CDX2. This newly found relationship permits specific drug screening assays as well as therapeutic and diagnostic methods.

10 Claims, 4 Drawing Sheets

SEQUENCE LISTING

```
<160> NUMBER OF SEQ ID NOS: 7

<210> SEQ ID NO 1
<211> LENGTH: 18
<212> TYPE: DNA
<213> ORGANISM: Homo sapiens

<400> SEQUENCE: 1
atggtgaggt ctgctccc                                              18

<210> SEQ ID NO 2
<211> LENGTH: 18
<212> TYPE: DNA
<213> ORGANISM: Homo sapiens

<400> SEQUENCE: 2
tctgctcccg gaccctcg                                              18

<210> SEQ ID NO 3
<211> LENGTH: 17
<212> TYPE: DNA
<213> ORGANISM: Homo sapiens

<400> SEQUENCE: 3
ggccatcctg gccggca                                               17

<210> SEQ ID NO 4
<211> LENGTH: 18
<212> TYPE: DNA
<213> ORGANISM: Homo sapiens

<400> SEQUENCE: 4
caccacccgc atcaccac                                              18

<210> SEQ ID NO 5
<211> LENGTH: 20
<212> TYPE: DNA
<213> ORGANISM: Homo sapiens

<400> SEQUENCE: 5
agtgaaaacc aggacgaaag                                            20

<210> SEQ ID NO 6
<211> LENGTH: 18
<212> TYPE: DNA
<213> ORGANISM: Homo sapiens
```

```
<400> SEQUENCE: 6
attgctctgc cgctgcag                                          18

<210> SEQ ID NO 7
<211> LENGTH: 19
<212> TYPE: DNA
<213> ORGANISM: Homo sapiens

<400> SEQUENCE: 7
gctcagcctg gaattgctc                                         19
```

CDX2 IS DOWNSTREAM MEDIATOR OF APC TUMOR SUPPRESSOR ACTIVITY

The U.S. government retains certain rights in this invention by virtue of its grants CA57345 and GM07814 to the inventors.

TECHNICAL FIELD OF THE INVENTION

This invention is related to the area of cancer. More particularly it is related to the area of genetic and biochemical targets involved in cancer development.

BACKGROUND OF THE INVENTION

Mutations in the adenomatous polyposis coli (APC) gene initiate the vast majority of human colorectal tumors (Kinzler and Vogelstein, 1996) but the functional consequences of such mutations at the biochemical level were until recently poorly understood. An important advance was made with the discovery that the APC gene product inhibits β-catenin/TCF regulated transcription (CRT) (Korinek et al., 1997, Morin et al., 1997). This inhibition is likely mediated by the binding of β-catenin to APC (Rubinfeld et al., 1993, Su et al., 1993), which facilitates phosphorylation of β-catenin by GSK-3β (Rubinfeld et al., 1996), and leads to its degradation through ubiquitination-dependent proteolysis (Munemitsu et al., 1995, Aberle et al., 1997, Orford et al., 1997). APC thus effectively regulates the cellular levels of β-catenin and consequently the formation of active transcription complexes between β-catenin and Tcf-4. Consistent with this model, alterations of β-catenin that render it refractory to regulation by APC were identified in a number of tumors with wild-type APC (Morin et al., 1997, Rubinfeld et al., 1996, Sparks et al., 1998), and it was shown that these β-catenin mutations as well as inactivating mutations of APC result in constitutive CRT (Morin et al., 1997). Accordingly, previous work had shown that all colorectal cancer cell lines tested had constitutive CRT (Korinek et al., 1997), suggesting that CRT deregulation is a key event in colorectal cancer initiation.

There is a continuing need in the art for identification of components of the CRT pathway and of other key pathways in the development of cancers.

SUMMARY OF THE INVENTION

It is an object of the present invention to provide methods for screening substances as candidate drugs for treating human cancers with mutant APC alleles.

It is another object of the present invention to provide methods of ameliorating the effects of APC mutations on human cells.

It is an object of the present invention to provide a method of preventing tumors in patients with Familial Adenomatous Polyposis.

Another object of the invention is to provide methods for detecting APC mutations.

These and other objects of the invention are achieved by providing one or more of the following embodiments. In one embodiment of the invention a method is provided for screening substances as candidate drugs for treating human cancers with mutant APC alleles. A human cell is contacted with a test substance. A CDX2 gene product selected from the group consisting of CDX2 mRNA and CDX2 protein is measured in the human cell. A test substance which increases expression in the cell of the CDX2 gene product is a candidate drug for treating human cancers with mutant APC alleles.

According to another embodiment of the invention a method is provided for screening substances as candidate drugs for treating human cancers with mutant APC alleles. A human cell is contacted with a test substance. A gene product of a CDX2-responsive gene is measured in the human cell. The gene product is selected from the group consisting of mRNA and protein. A test substance which increases expression in the cell of the CDX2-responsive gene product is a candidate drug for treating human cancers with mutant APC alleles.

According to still another embodiment a method is provided for screening substances as candidate drugs for treating human cancers with mutant APC alleles. A human cell comprising a CDX2-responsive reporter construct is contacted with a test substance. A gene product of the reporter construct selected from the group consisting of mRNA and protein is measured. A test substance which increases expression in the cell of the reporter is a candidate drug for treating colorectal cancer.

Yet another aspect of the invention is a method of ameliorating the effects of APC mutations on human cells. A human wild-type CDX2 coding sequence is administered to human cells comprising mutant APC alleles. As a result, expression of CDX2 is upregulated.

Still another aspect of the invention is a method of preventing tumors in patients with Familial Adenomatous Polyposis. A human wild-type CDX2 coding sequence is administered to intestinal cells of a human with Familial Adenomatous Polyposis. As a result, expression of CDX2 is upregulated in the intestinal cells, thereby preventing or reducing the incidence of formation of tumors in the human.

According to still another embodiment of the invention a method is provided for detecting APC mutations. Expression of a human CDX2 gene product selected from the group consisting of CDX2 mRNA and CDX2 protein, is measured in a test sample comprising human cells. The measured expression in the test sample is compared to expression in a normal human control sample. Diminished expression of the human CDX2 gene product in the test sample relative to the normal control sample suggests that the test sample comprises mutant APC alleles.

Another diagnostic aspect of the invention is a method for detecting APC mutations. Expression of a human CDX2-responsive gene product selected from the group consisting of mRNA and protein, is measured in a test sample. The measured expression in the test sample is compared to expression in a nomal control sample. Diminished expression of the human CDX2-responsive gene product in the test sample relative to the nomal control sample suggests that the test sample comprises mutant APC alleles.

Another diagnostic embodiment of the invention provides a method for detecting APC mutations. Expression of a human CDX2-responsive reporter gene product selected from the group consisting of mRNA and protein in a test sample comprising human cells is measured. The measured expression in the test sample is compared to expression in a nomal human control sample. Diminished expression of the human CDX2-responsive reporter gene product in the test sample relative to the nomal human control sample suggests that the test sample comprises mutant APC alleles.

These and other embodiments of the invention which are described in more detail below provide the art with a new therapeutic target for fighting cancers.

BRIEF DESCRIPTION OF THE DRAWINGS

FIG. 1 shows CRT activity in cancer cell lines. The indicated cell lines were transfected with luciferase reporter constructs containing three consensus (TCF-Luc) or mutant (TCF*-Luc) TCF-binding sites, plus a CMV-driven β-galactosidase (β-gal) reporter to control for transfection efficiency. Twenty-four hours later, the cells were collected and luciferase and β-gal activities determined. Bars represent average luciferase activities normalized to the values obtained with TCF*-Luc. SW480, HCT116 and RKO are human colorectal cancer (CRC) lines. CRT activity in HeLa, a human cervical cancer line, is typical for non-CRC lines (Korinek et al. 1997). The status of APC and β-catenin in each line is indicated (NL, no abnormalities detected; MUT, mutant; ND, not determined). Details of the construction of the TCF-Luc and TCF*-Luc reporters are available upon request. The pCMVβ vector (Clontech) was used as the CMV-driven β-galactosidase (β-gal) reporter control. Cell lines were maintained in McCoy's medium (Life Technologies, Gaithersburg, Md.) supplemented with 10% fetal bovine serum and antibiotics. Transfections were performed on 24-well tissue culture plates when cells were 40 to 60% confluent using Lipofectamine (Life Technologies), or FuGENE6 (Boehringer-Mannheim) according to the manufacturer's instructions. Cells were collected and luciferase and β-galactosidase activities determined using the Luciferase Assay Reagents kit (Promega) and the Aurora GAL-XE Kit (ICN), respectively.

FIG. 2 demonstrates mutational analysis of CDX2 and the APC pathway in RKO. Autoradiograph of a sequencing gel showing the 4 bp deletion in the cDNA of RKO. Sequencing reactions were performed directly on the RT-PCR product (RKO) and on two clones are shown. Cloning of the RT-PCR product yielded clones with wild-type (WT) or mutant (RKO( )) sequence. The complete coding region of CDX2 was amplified using primers CDX2-0039F and CDX2-1047R. The PCR products were purified by isopropanol precipitation and sequenced with primers CDX2-0048F, CDX2-0252F, CDX2-0413F, CDX2-0604F and CDX2-1035R (Table 1) as described below. APC, β-catenin, and TCF-4 did not display mutations (data not shown). Western blot analysis of APC in RKO was performed as previously described and revealed apparently full-length APC protein. Since it was possible that mutations resulting in very late truncations could be missed by western blotting, codons 2230 through the carboxyl-terminus of APC were analyzed by direct sequencing as described. For β-catenin analysis, a genomic PCR fragment including codon 1 in exon 2 to codon 90 in exon 4 and encompassing the N-terminal regulatory region was amplified as described. PCR products were gel-purified and sequenced directly using ThermoSequenase (Amersham) and $^{33}$P-labeled ddNTP's (Amersham) according to the manufacturer's instructions. The TCF-4 transcript was amplified by RT-PCR in two segments and its entire coding region excluding codons 1–16 was sequenced. Purification of genomic DNA and RNA, PCR, and RT-PCR were performed as described.

FIG. 3 shows transcription activity of wild type and mutant CDX2. SW480 cells were transfected with a luciferase reporter gene (0.5 ug) under control of a fragment of the Sucrase-Isomaltase (SI-Luc) or the CDX2 (CDX-Luc) promoter, an effector construct (2.0 ug) with CMV-driven wild-type (WT), mutant (MUT) or no (Vector) CDX2 genes, and CMV-driven β-galactosidase (β-gal) to control (0.5 ug) for transfection efficiency. Forty-eight hours later, the cells were collected and luciferase and β-gal activities determined as described in FIG. 1. The SI-Luc reporter was derived from TCF-Luc by replacing the PstI-XbaI fragment containing the TCF-binding sites with a CDX2-responsive fragment of the Sucrase-Isomaltase gene promoter. (Wu et al. 1992) CDX-Luc was created from pGL3 -Basic (Clontech) by inserting a 9 kb bp XhoI genomic DNA restriction fragment from the CDX2 promoter, with its 3'end 200 bp downstream from the presumed transcription start site. Bars represent the average luciferase activities normalized to the vector control.

FIG. 4 shows CDX2 regulation by APC. RNA was purified from cells lines HT29-APC and HT29-GAL at the indicated times after induction. Twenty µg of total RNA from normal colon and 30 µg from each cell line were used in RNase protection assays (RPA) with probes derived from the 3'-untranslated region of the human CDX2 gene (top) or EF-1α (as a control). Asterisks indicate nonspecific bands. HT29-APC and HT29-GAL cells contain zinc-inducible APC and β-gal genes, respectively. Cells were plated at 40–50% confluency, induced two days later with 120 µM $ZnCl_2$ and harvested at the indicated times after induction. Total RNA was prepared using Promega's RNA isolation kit following the manufacturer's instructions. A PstI restriction fragment containing nucleotides 1018 to 1346 of CDX2 cDNA (GENBANK accession number U51096) inserted into pZero (Invitrogen) in the anti-sense orientation respective to the T7 promoter was used as template to prepare the RNase protection probe. Probe synthesis and RNase protection assays were carried out using the Ambion RNase protection assay kit following the manufacturer's instructions.

DETAILED DESCRIPTION OF THE INVENTION

The present invention flowed from the surprising observation that β-catenin/TCF regulated transcription (CRT) is absent in RKO, a widely studied colorectal cancer cell line (Brattain et al., 1984). We found that RKO contains a mutant CDX2 gene, and that CDX2 transcription is induced by APC. These results suggest a connection between APC and CDX2 in colorectal cancers and raise the possibility that CDX2 is one of the mediators of APC's tumor-suppressing activity. CDX2 has been recently implicated in intestinal tumorigenesis in mice (Chawengsaksophak et al. 1997).

The induction of CDX2 expression by APC permits a number of drug screening assays to be performed. In each of the assays, a human cell is contacted with a test substance, and its effect on CDX2-driven expression is monitored. The human cell may have wild-type or mutant APC alleles, or it may be heterozygous. Expression can be monitored by measuring either mRNA or protein synthesis. Any of the many means known in the art for measuring a particular mRNA species or particular protein can be used. Such techniques include without limitation, immunological techniques such as Western blots and ELISA, and hybridization based techniques such as Northern blots.

CDX2-driven expression can be monitored by measuring any gene product which is regulated by CDX2. These include CDX2 protein and mRNA (Mallo et al., 1997), the gene product of any CDX2-responsive gene, including but not limited to sucrase isomaltase, and a gene product of a CDX2-responsive reporter gene construct. As shown below, CDX2 autoregulates its own transcription, as well as regulating the transcription of other genes. Reporter gene constructs are known in the art and employ a gene (the reporter) with an easily detectable gene product, such as luciferase, green fluorescent protein, or β-galactosidase, placed downstream from a promoter or enhancer which comprises a CDX2-binding region. (Levy et al., 1995) Binding of CDX2 positively regulates the transcription from the promoter.

Test substances which are found to increase the expression of the monitored CDX2-responsive genes are candidate therapeutic agents for treating human cancers, in particular cancers which have mutant APC alleles. Such drugs are also useful for treating Familial Adenomatous Polyposis (FAP) patients to prevent the development of frank tumors.

Given the functional relationship of CDX2 and APC, increasing CDX2 expression in tumor cells or cells predisposed to becoming cancerous can help to ameliorate the effects of APC mutations. One way to accomplish such increased expression of APC is to treat cells with one or more APC mutations with wild-type human CDX2-encoding polynucleotides. Increasing the gene-dosage of CDX2 upregulates CDX2. This results in decreased incidence or risk of cancer development in FAP-affected individuals and amelioration of tumor growth and development in tumor-bearing individuals.

Based on the discovery of the regulation of CDX2 transcription by APC, a number of diagnostic assays have been developed. These assays are based on the use of CDX2 expression as an indicator of the mutational status of APC. Any means of monitoring CDX2 expression can be used, whether based on mRNA or protein. CDX2 itself can be monitored, or a CDX2 regulated gene can be monitored. Alternatively a CDX2-responsive reporter gene can be monitored. Typically expression of the CDX2 expression product is measured in a test sample and compared to that in a control sample of normal cells or tissue. Preferably the samples are matched as closely as possible, i.e., from the same organ type and the same individual. Diminished expression in the test sample relative to the control sample suggests a mutation in APC. Other confirmatory tests can be performed as well, which may involve direct testing of APC.

In summary, we have shown that the RKO cell line contains wild type APC, CTNNB1 and TCF-4 genes. RKO is the first human colorectal cancer cell line shown to lack constitutive β-catenin regulated transcription, and it contains an inactivating mutation of the CDX2 gene. In this regard, it is interesting that Wicking and co-workers (Wicking et al., 1998) recently reported a case of a replication error-prone (RER+) colorectal cancer with mutations in both alleles of CDX2. As RKO is also mismatch repair deficient, mutations in this cell line must be regarded with caution. However, the CDX2 mutation in RKO was shown to functionally inactivate the gene product through experiments with two completely different reporters. We also show that restoring expression of full-length APC in a human colorectal cancer cell line can induce CDX2 expression. Finally, we have shown that CDX2 can positively regulate its own expression. Taken together, the data suggest the following model for colon cancer initiation. In most cases, the normal down-regulation of β-catenin/TCF by APC is abrogated by mutations in either APC or β-catenin, leading to constitutive transcription of β-catenin/TCF-responsive genes and indirectly to a variety of gene expression alterations, including up-regulation of c-MYC (He et al. 1998) and abnormally low levels of CDX2 expression. It is important to note that, unlike c-MYC, the effects of APC on CDX2 can not be mediated directly through β-catenin/TCF since APC induces CDX2 rather than repressing it. The link between APC and CDX2, even if mediated by the β-catenin/TCF pathway, will therefore require additional cellular factors that directly affect CDX2 expression. In rare cases, such as in RKO, the APC/β-catenin pathway is intact and neoplastic growth may result through one or more direct "hits" within APC-regulated genes, including CDX2. Although simple dosage affects, complete loss of function, or unrealized dominant negative affects can not be ruled out for some CDX2 mutations, they can't readily account for the tumor development in the CDX2+/− mice (Chawengsaksophak et al., 1997). One possible explanation for the mouse observations and the alteration observed in RKO is that the effects of a CDX2 alteration may be exacerbated by interruption of a positive feedback loop which normally controls its expression. The resulting reduced expression of CDX2 could be expected to compromise the normal process of terminal differentiation in the colonic epithelium, given that CDX2 can induce differentiation of intestinal epithelial cells (Suh et al. 1996). This scenario is consistent with the published data in humans and rodents, including the observations that intestinal adenomas of Apc mutant mice (Chawengsaksophak et al., 1997), chemically induced rodent tumors (Ee et al. 1995) and human colorectal tumors (Ee et al. 1995, Mallo et al., 1997) have abnormally low levels of CDX2 expression.

The above disclosure generally describes the present invention. A more complete understanding can be obtained by reference to the following specific examples which are provided herein for purposes of illustration only, and are not intended to limit the scope of the invention.

EXAMPLE 1

β-catenin Regulated Transcription Activity in Cancer Cell Lines

Figure 1:
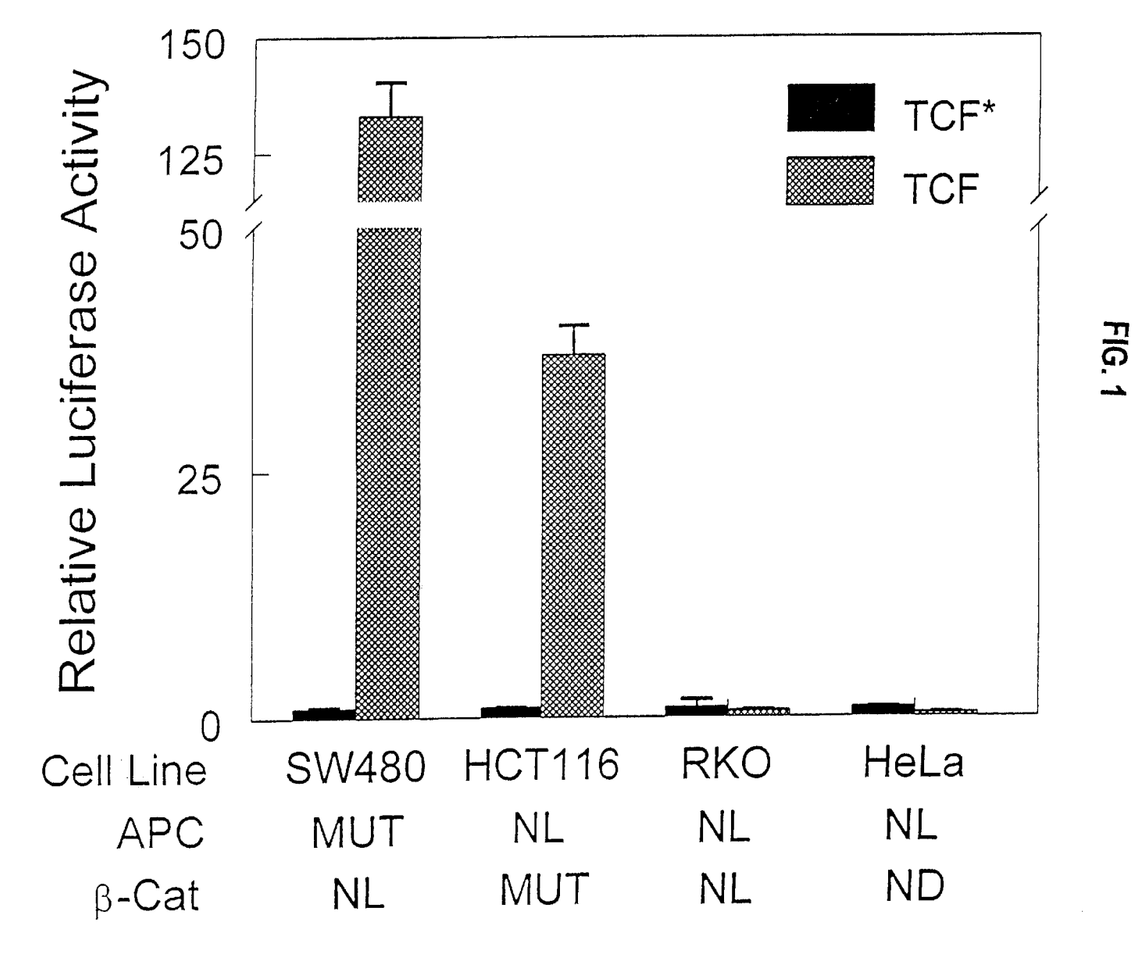

Constitutive activation of β-catenin regulated transcription has been reported in all colorectal cancer cell lines tested, a feature that distinguishes them from cancer cell lines derived from other tissue types (examples in FIG. 1). CRT is typically measured using luciferase reporters called TOPFLASH and FOPFLASH, which contain promoters with several copies of a normal or mutant version of a TCF-response element (Korinek et al., 1997), respectively. Activation of CRT results in a high ratio of TOPFLASH to FOPFLASH luciferase activity. Surprisingly, when we measured CRT in RKO, we found that the levels of luciferase activity were similar with both TOPFLASH and FOP-FLASH reporters. However, we also observed that the levels of FOPFLASH reporter activity were significantly higher in RKO than in the other cancer cell lines tested. We were therefore unable to conclude that RKO lacked constitutive CRT activity, as it was possible that it was simply masked by high background activity of the FOPFLASH control in this particular cell line. To distinguish between these two possibilities, we constructed a new pair of CRT reporter vectors (TCF-Luc and TCF*-Luc) that displayed much lower background activities in all lines tested. We then repeated our analysis of CRT activity in RKO using these vectors and demonstrated that RKO lacked constitutive βcatenin regulated transcription (FIG. 1). We further determined that this was not due to an intrinsic inability to activate TCF-responsive elements, since TCF-Luc, but not TCF*-Luc, could be activated in RKO by co-transfection with a plasmid encoding βcatenin/S33Y (Morin et al. 1997), a constitutively active mutant βcatenin.

EXAMPLE 2

Genetic Analysis of RKO

Figure 2:
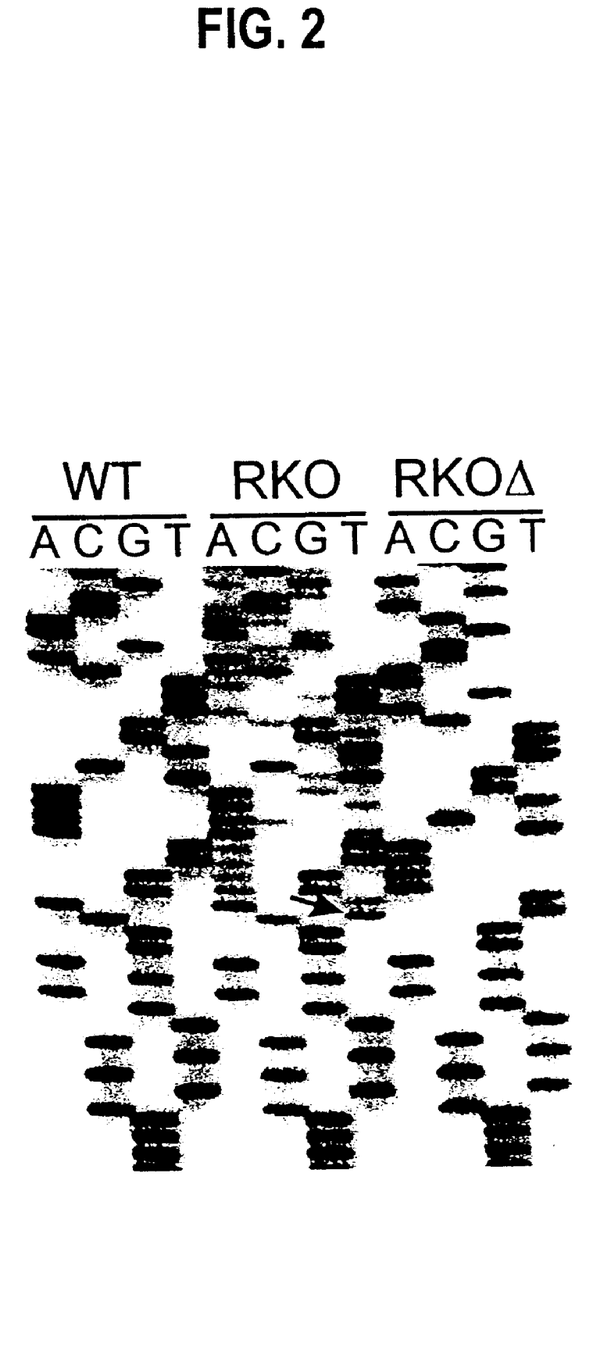

Because exceptional cases are often of considerable heuristic value, we decided to investigate RKO in greater detail. As expected from the above results, mutational analyses of the βcatenin (CTNNB1), Tcf-4 and APC genes revealed no CRT-activating alterations. We thus suspected that mutation of a downstream component of the pathway might have substituted for APC inactivation in this line. In particular, we were intrigued by the report that Cdx2+/− mice develop multiple adenomatous polyps in the colon (Chawengsaksophak et al. 1997). As multiple intestinal tumors in mice had previously been routinely observed only in Apc+/− animals (Su et al. 1997, Fodde et al. 1994), this observation raised the possibility that CDX2 might play a role in the initiation of human colorectal tumors as well. Sequencing of the coding region of CDX2 indeed revealed a heterozygous 4 base-pair deletion (AGGCAGG to AGG) within the sequence corresponding to helix 3 of the CDX2 homeodomain (FIG. 2). The predicted abnormal protein lacked the carboxyl-terminal 85 amino acids, including a major part of the DNA-binding domain. These were substituted with 45 new residues and the protein was predicted to be transcriptionally inactive. Interestingly, no mutation in the remaining allele of CDX2 was detected in RKO cells. Similarly, no loss or alterations of the wild-type Cdx2 allele were found in colon tumors developing in Cdx2+/− mice (Chawengsaksophak et al. 1997).

TABLE 1

Oligonucleotide Primers used for Mutational Analysis of CDX2

| Name | Oligonucleotide Sequence (5' to 3') | |
|---|---|---|
| CDX2-0039F | ATGGTGAGGTCTGCTCCC | (SEQ ID NO:1) |
| CDX2-0048F | TCTGCTCCCGGACCCTCG | (SEQ ID NO:2) |
| CDX2-0252F | GGCCATCCTGGCCGGCA | (SEQ ID NO:3) |
| CDX2-0413F | CACCACCCGCATCACCAC | (SEQ ID NO:4) |
| CDX2-0604F | AGTGAAAACCAGGACGAAAG | (SEQ ID NO:5) |
| CDX2-1035R | ATTGCTCTGCCGCTGCAG | (SEQ ID NO:6) |
| CDX2-1047R | GCTCAGCCTGGAATTGCTC | (SEQ ID NO:7) |

To test the hypothesis that the mutation in CDX2 functionally altered its transcriptional activation capabilities, we constructed plasmids encoding wild-type (CMV-CDX-WT) or mutant (CMV-CDX-MUT) CDX2 genes under control of a CMV promoter-enhancer, as well as reporter vectors containing Luciferase under control of a CDX2-responsive promoter (SI-Luc) (Suh et al 1994). Co-transfection experiments showed that CMV-CDX-WT, but not CMV-CDX-MUT could activate transcription of the reporter constructs (FIG. 3), formally demonstrating that the CDX2 mutation in RKO inactivated the gene product.

EXAMPLE 3
CDX2 Regulation by APC

Figure 4:
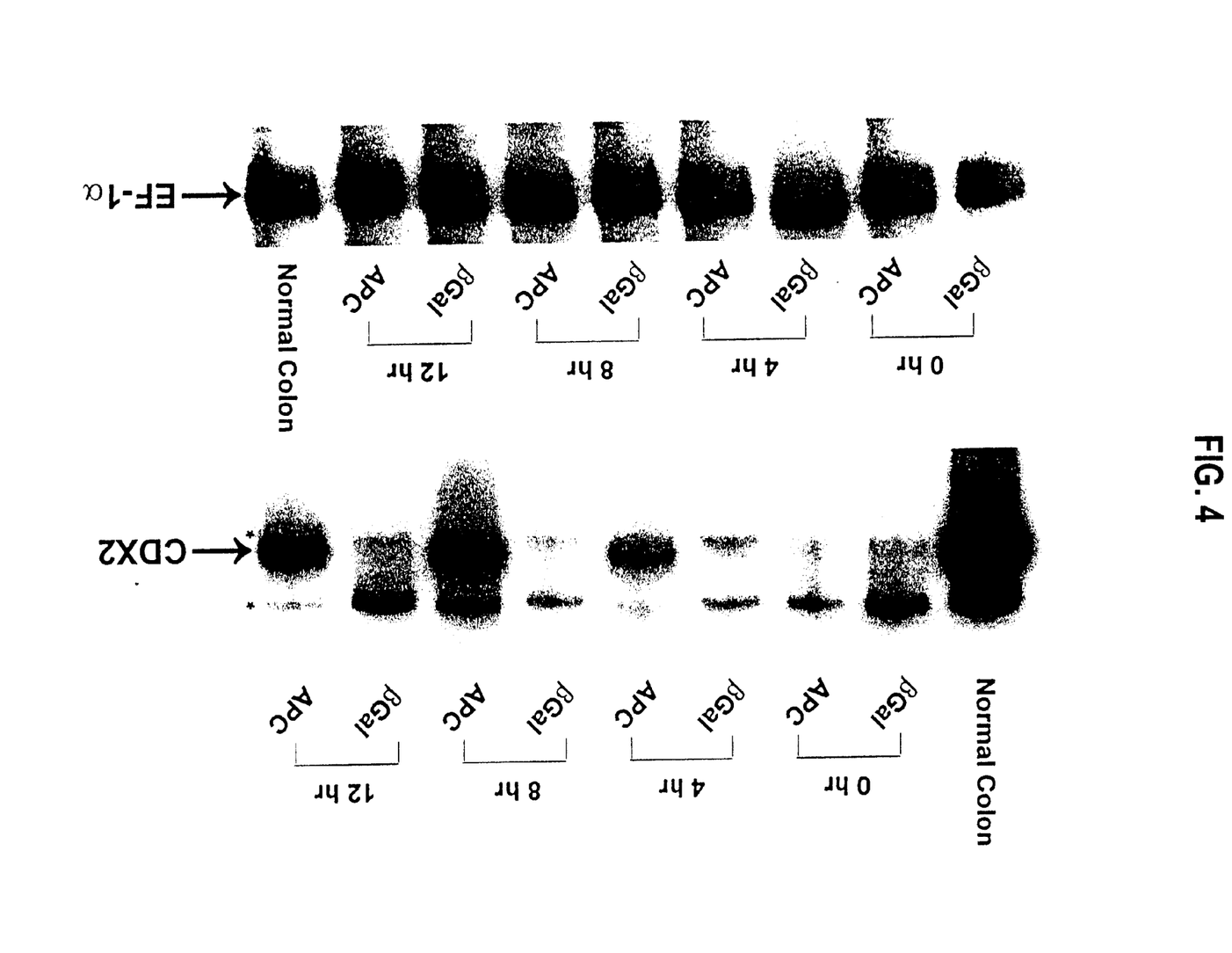

The occurrence of a CDX2 mutation in a tumor cell line with wild-type APC and without CRT activity suggested that there might be a connection between APC and CDX2 in human cancer, and in particular that CDX2 might be one of the effectors of APC's tumor-suppressing activity. Alternatively, CDX2 and APC could both behave as tumor suppressor genes independently of one another (He et al., 1997). To begin to distinguish between these two possibilities, we investigated whether APC could regulate the levels of CDX2 RNA. HT29-APC and HT29-GAL are paired colorectal cancer cell lines that contain zinc-inducible wild-type APC or β-galactosidase genes, respectively (Morin et al. 1996). The endogenous APC genes in HT29 cells are mutant. Upon Zinc induction, HT29-APC, but not HT29-GAL, express wild type APC, which inhibits the interaction between β-catenin and Tcf-4 and consequently downregulates CRT activity. Total RNA was collected from HT29-APC and HT29-GAL cells at different time points after Zinc induction (Morin et al. 1996, He et al. 1998) and RNase protection assays were performed on these samples with a probe derived from the 3'-untranslated region of CDX2. As shown in FIG. 4, induction of APC was associated with a rapid and significant increase in the level of CDX2 RNA.

EXAMPLE 4
Autoregulation of CDX2 Expression

Figure 3:
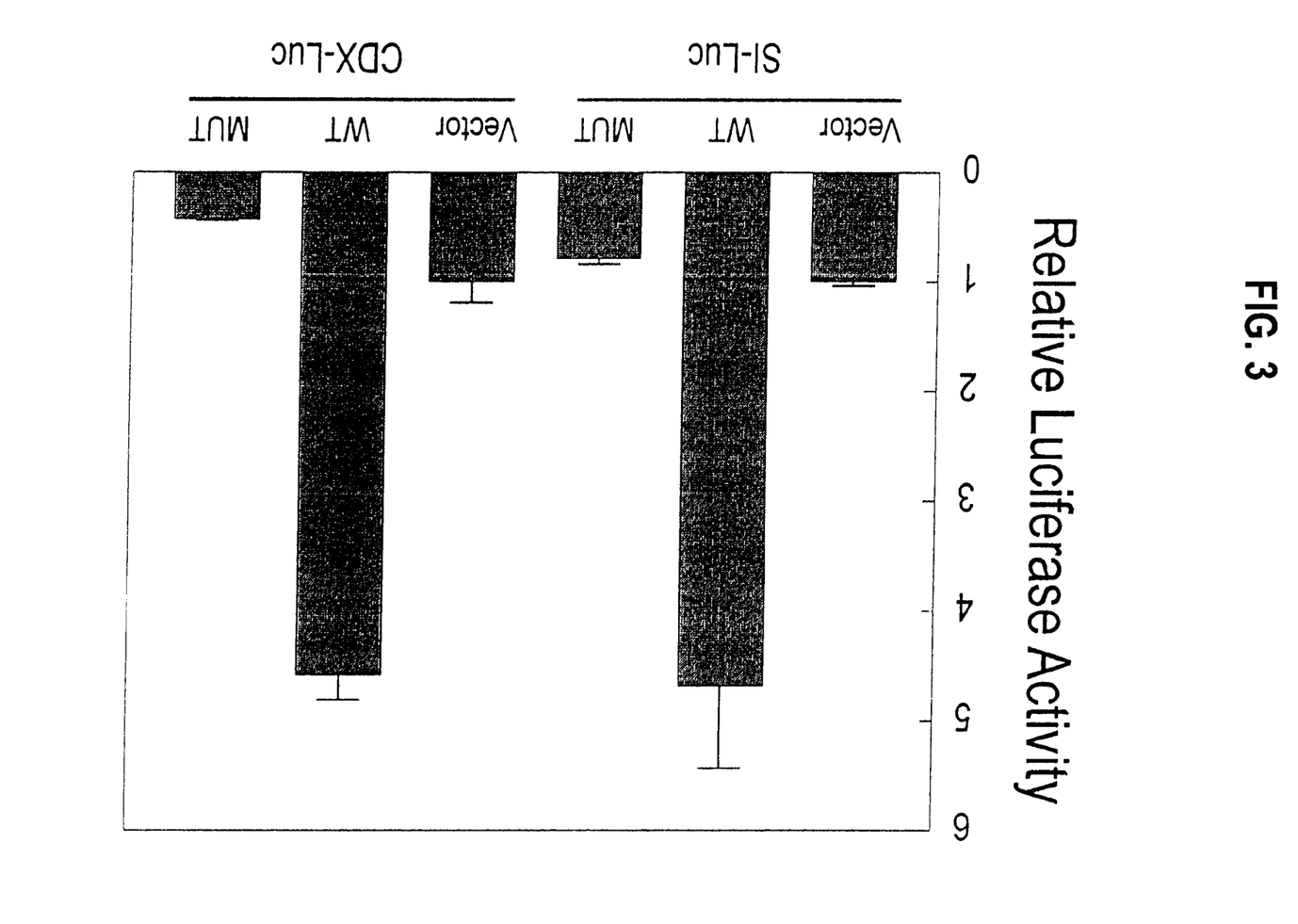

In addition to developing colonic tumors, Chawengsaksophak and co-workers (Chawengsaksophak et al. ,1997) reported that Cdx2+/− mice suffer from a variety of developmental abnormalities that display a homeotic character. These fall into well-defined categories, but differ significantly from animal to animal, suggesting that they depend on a stochastic event. Furthermore, the remaining wild-type allele is not expressed in the mouse intestinal tumors that develop. How could loss of one allele of Cdx2 result in reduced expression of the remaining, wild-type allele? We postulated that this would be possible if the level of expression of Cdx2 was regulated, in part, by Cdx2 itself, thereby operating through a positive feedback loop. To test this possibility, we constructed a reporter vector in which the luciferase gene was driven by a fragment of the human CDX2 gene promoter (CDX-Luc). As shown in FIG. 3, CDX-Luc could be specifically activated by wild-type CDX2, but not by the mutant CDX2 protein found in RKO cells, suggesting that the CDX2 protein indeed contributes to its own expression through autoregulation.

All cited references are expressly incorporated herein.

REFERENCES

Aberle H, Bauer A, Stappert J, Kispert A, and Kemler R. (1997). *EMBO J.*, 16, 3797–3804.

Chawengsaksophak K, James R, Hammond V E, Kontgen F and Beck F (1997). *Nature*, 386, 84–87.

Ee H C, Erler T, Bhathal P S, Young G P and James R J (1995). *Am. J Pathol.*, 147, 586–592.

Eshleman, J. R., Lang, E. Z., Bowerfind, G. K., Parsons, R., Vogelstein, B., Willson, J. K., Veigl, M. L., Sedwick, W. D. & Markowitz, S. D. (1995). *Oncogene*, 10, 33–37.

Morin, P. J., Vogelstein, B. & Kinzler, K. W. (1996). *Proc Natl Acad Sci USA*, 93, 7950–7954

Fodde R, Edelmann W, Yang K, van Leeuwen C, Carlson C, Renault B, Breukel C, Alt E, Lipkin M, Khan P M and Kucherlapati R (1994). *Proc. Natl. Acad. Sci. USA*, 91, 8969–8973.

He T-C, Sparks A B, Rago C, Hermeking H, Zawel L, da Costa L T, Morin P J, Vogelstein B and Kinzler K W (1998). *Science*, 281, 1509–1512.

He T C, da Costa L T, Thiagalingam S. (1997). *Bioessays* 19, 551–555.

Kinzler K W and Vogelstein B. (1996). *Cell*, 87, 159–170.

Korinek V, Barker N, Morin P J, van Wichen D, de Weger R, Kinzler K W, Vogelstein B and Clevers H. (1997). *Science*, 275, 1784–1787.

Levy T E, S Suh, S Siang, and P G Traber (1995). *Gastroenterology*, 108:A301

Mallo G V, Rechreche H, Frigerio J M, Rocha D, Zweibaum A, Lacasa M, Jordan B R, Dusetti N J, Dagorn J C, Iovanna J L. (1997). *Int. J. Cancer*, 74, 35–44.

Morin P J, Vogelstein B and Kinzler K W (1996). *Proc. Natl. Acad. Sci. USA*, 93, 7950–7954.

Morin P J, Sparks A B, Korinek V, Barker N, Clevers H, Vogelstein B and Kinzler K W. (1997). *Science.* 275, 1787–1790.

Munemitsu S, Albert I, Souza B, Rubinfeld B and Polakis P. (1995). *Proc. Natl. Acad. Sci. USA*, 92, 3046–3050.

Powell S M, Zilz N, Beazer-Barclay Y, Bryan T M, Hamilton S R, Thibodeau S N, Vogelstein B and Kinzler K W (1992). *Nature*, 359, 235–237.

Orford K, Crockett C, Jensen J P, Weissman A M, and Byers S W. (1997). *J. Biol. Chem.,* 272, 24735–24738.

Riggins G J, Markowitz S, Wilson J K, Vogelstein B and Kinzler K W. (1995). *Cancer Research,* 55, 5184–5186.

Rubinfeld B, Souza B, Albert I, Muller O, Chamberlain S H, Masiarz F R, Munemitsu S and Polakis P. (1993). *Science,* 262, 1731–1734.

Rubinfeld B, Albert I, Porfiri E, Fiol C, Munemitsu S and Polakis P (1996). *Science,* 272, 1023–1025.

Rubinfeld B, Robbins P, El-Gamil M, Albert I, Porfiri E and Polakis P. (1997). *Science,* 275, 1790–1792.

Smith K J, Johnson K A, Bryan T M, Hill D E, Markowitz S, Willson J K, Paraskeva C, Petersen G M, Hamilton S R, Vogelstein B and Kinzler K W (1993). *Proc. Nat. Acad. Sci. USA,* 90, 2846–2850.

Sparks A B, Morin P J, Vogelstein B and Kinzler K W (1998). *Cancer Research,* 98, 1130–1134.

Su L K, Kinzler K W, Vogelstein B, Preisinger A C, Moser A R, Luongo C, Gould K A and Dove W F (1992). *Science,* 256, 668–670.

Su L K, Vogelstein B and Kinzler K W. (1993). *Science,* 262, 1734–1737.

Suh E, Chen L, Taylor J, and Traber P G (1994). *Mol. Cell. Biol.,* 14, 7340–7351.

Suh E and Traber P G (1996). *Mol. Cell. Biol.,* 16, 619–625.

Wicking C, Simms L A, Evans T, Walsh M, Chawengsak-sophak K, Beck F, Chenevix-Trench G, Young J, Jass J, Leggett B, Wainwright B. (1998). *Oncogene,* 17, 657–659.

Wu G D, W Wang, P G Traber (1992). *J. Biol. Chem.* 267:7863–7870

We claim:

1. A method for screening substances as candidate drugs for treating human cancers associated with mutant APC alleles, comprising the steps of:

contacting a human cell with a test substance;

measuring a CDX2 gene product selected from the group consisting of CDX2 mRNA and CDX2 protein in the human cell;

identifying a test substance which increases expression in the cell of the CDX2 gene product as a candidate drug for treating human cancers with mutant APC alleles.

2. The method of claim 1 wherein the human cell comprises mutant APC alleles.

3. The method of claim 1 wherein the gene product is mRNA.

4. The method of claim 1 wherein the gene product is protein.

5. A method for screening substances as candidate drugs for treating human cancers associated with mutant APC alleles, comprising the steps of:

contacting a human cell with a test substance;

measuring a gene product of a sucrase-isomaltase gene in the human cell, wherein the gene product is selected from the group consisting of mRNA and protein; and identifying a test substance which increases expression in the cell of the gene product of the surcrase-isomaltase gene as a candidate drug for treating human cancers with mutant APC alleles.

6. The method of claim 5 wherein the gene product is mRNA.

7. The method of claim 5 wherein the gene product is protein.

8. A method for screening substances as candidate drugs for treating human cancers associated with mutant APC alleles, comprising the steps of:

contacting a human cell comprising a CDX2-responsive reporter construct, which comprises a transcriptional regulatory region of a sucrase-isomaltase gene, with a test substance;

measuring a gene product of the reporter construct selected from the group consisting of mRNA and protein; and identifying a test substance which increases expression in the cell of the reporter as a candidate drug for treating human cancers with mutant APC alleles.

9. The method of claim 8 wherein the gene product is mRNA.

10. The method of claim 8 wherein the gene product is protein.

* * * * *